(12) United States Patent
Kleiner et al.

(10) Patent No.: US 9,056,155 B1
(45) Date of Patent: Jun. 16, 2015

(54) COATINGS HAVING AN ELASTIC PRIMER LAYER

(75) Inventors: Lothar W. Kleiner, Los Altos, CA (US); Yiwen Tang, San Jose, CA (US); Mikael O. Trollsas, San Jose, CA (US); Syed F. A. Hossainy, Fremont, CA (US); Santosh Prabhu, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1300 days.

(21) Appl. No.: 11/807,833

(22) Filed: May 29, 2007

(51) Int. Cl.
| | |
|---|---|
| A61L 31/00 | (2006.01) |
| A61L 27/34 | (2006.01) |
| A61L 27/54 | (2006.01) |
| C08L 67/02 | (2006.01) |
| A61L 31/10 | (2006.01) |

(52) U.S. Cl.
CPC ............... *A61L 31/10* (2013.01); *A61L 27/34* (2013.01); *A61L 27/54* (2013.01); *C08L 67/02* (2013.01); *A61L 2300/00* (2013.01)

(58) Field of Classification Search
None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,632,776 A * | 5/1997 | Kurumatani et al. ......... 424/423 |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

Jokhadze (Journal of Biomaterials Science Polymer edition 2007 18:411-438.*
Stella A Case for Prodrugs in Prodrugs: Challenges and Rewards Part I Eds. Stella et al. New York: Springer, 2007. 1-33.*
Zhou et al. Biomaterials 2003 24:3563-3570.*
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).

(Continued)

*Primary Examiner* — Juliet Switzer
*Assistant Examiner* — Caralynne Helm
(74) *Attorney, Agent, or Firm* — Squire Patton Boggs (US) LLP (57) ABSTRACT

Provided herein is a coating an elastic primer layer and the method of making and using the same.

10 Claims, 2 Drawing Sheets

(56) References Cited

U.S. PATENT DOCUMENTS

| | | |
|---|---|---|
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A * | 11/2000 | Hossainy et al. ............. 427/2.3 |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,475,779 B2 | 11/2002 | Mathiowitz et al. |
| 6,482,834 B2 | 11/2002 | Spada et al. |
| 6,494,862 B1 | 12/2002 | Ray et al. |
| 6,503,538 B1 * | 1/2003 | Chu et al. ............. 424/497 |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,534,089 B1 * | 3/2003 | Ayer et al. ............. 424/473 |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,613,432 B2 | 9/2003 | Zamora et al. |
| 6,616,765 B1 | 9/2003 | Hossaony et al. |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,641,611 B2 | 11/2003 | Jayaraman |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,689,350 B2 | 2/2004 | Uhrich |
| 6,695,920 B1 | 2/2004 | Pacetti et al. |
| 6,703,040 B2 * | 3/2004 | Katsarava et al. ............. 424/444 |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,730,064 B2 | 5/2004 | Ragheb et al. |
| 6,733,768 B2 | 5/2004 | Hossainy et al. |

(56) References Cited

U.S. PATENT DOCUMENTS

| | | |
|---|---|---|
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 * | 6/2004 | Pacetti ............ 428/212 |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Falotico et al. |
| 6,780,424 B2 | 8/2004 | Claude |
| 6,790,228 B2 | 9/2004 | Hossainy et al. |
| 6,824,559 B2 | 11/2004 | Michal |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 7,008,667 B2 | 3/2006 | Chudzik et al. |
| 7,094,256 B1 * | 8/2006 | Shah et al. ............ 623/1.46 |
| 7,316,710 B1 * | 1/2008 | Cheng et al. ............ 623/1.15 |
| 2001/0007083 A1 | 7/2001 | Roorda |
| 2001/0029351 A1 | 10/2001 | Falotico et al. |
| 2001/0037145 A1 | 11/2001 | Guruwaiya et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0025799 A1 * | 2/2005 | Hossainy et al. ............ 424/423 |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0059984 A1 * | 3/2005 | Chanduszko et al. ........ 606/151 |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2005/0131201 A1 * | 6/2005 | Pacetti et al. ............ 528/272 |
| 2006/0093842 A1 * | 5/2006 | DesNoyer et al. ......... 428/474.4 |
| 2006/0136048 A1 * | 6/2006 | Pacetti et al. ............ 623/1.42 |
| 2006/0147491 A1 * | 7/2006 | DeWitt et al. ............ 424/426 |
| 2006/0165762 A1 * | 7/2006 | Plaut et al. ............ 424/445 |
| 2009/0276036 A1 * | 11/2009 | Nagura et al. ............ 623/1.44 |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| EP | 1 407 786 | 3/2006 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |

(56) References Cited

FOREIGN PATENT DOCUMENTS

| | | |
|---|---|---|
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Bird et al, *Dynamics of Polymeric Liquids*, vol. 1, A Wiley-Interscience Publication, pp. 139-153, (1987).

ChemFiles, Unnatural Amono Acids II, vol. 2, No. 4, 20 pgs. (2002).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Fried, *Polymer Science and Technology*, Chapter 11.2, Introduction to Polymer Rheology, pp. 439-448 (2003).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

va Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

COATINGS HAVING AN ELASTIC PRIMER LAYER

BACKGROUND OF THE INVENTION

1. Field of the Invention

This invention generally relates to a coating having a primer layer that includes at least one elastic polymer.

2. Description of the Background

Stents are used not only as a mechanical intervention of vascular conditions but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA (Percutaneous Transluminal Coronary Angioplasty) procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Polymeric coatings have been used for local delivery therapeutic substances to a leision site via, e.g., stenting. A polymer with groups compatible with the surface of a medical device, e.g., ester group, will have a good adhesion when coated on top of the device. When a polymer has a right glass transition temperature ($T_g$), right molecular weight, it can used to form a primer layer for a coating. However, even one uses a polymer layer with good adhesion to the surface of a device, delamination or cracking can occur upon deploying the device, e.g., stent expansion.

The embodiments of the present invention provide for methods addressing these issues.

SUMMARY OF THE INVENTION

Provided herein is a coating on a medical device, such as a stent, that includes a construct having an elastic primer layer. The elastic primer layer will lower the stress generated in the coating, e.g., stress generated in the drug depot layer (which is also referred to as drug reservoir layer). An elastic primer layer can absorb more of elastic strain energy upon deployment of the medical device, e.g., stent expansion, and therefore shield the more brittle part of the coating from the stress. This construct therefore will minimize or eliminate the cracking in the coating (e.g., the matrix layer or the drug depot layer). In addition, interfacial shear stress between the drug depot layer and the surface of the medical device, had the depot layer been directly deposited on the surface for the medical device, and thus, the use of an elastic layer will minimize or eliminate the occurrence of drug depot layer delamination.

In some embodiments, the depot system can be a pure active agent without a polymeric carrier. When this design is used, usually it is hard to coat the bioactive itself onto a metal surface of the depot system, e.g., the depot system can have cracking. Applying an elastic layer onto the metal surface, and then applying to the elastic layer the pure bioactive agent can form the depot system without causing further cracking of the coating.

The drug depot layer can include any bioactive agent. In some embodiments, the bioactive agents can be paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl(4-amino-TEMPO), tacrolimus, dexamethasone, rapamycin, rapamycin derivatives, 40-O-(2-hydroxyl)ethyl-rapamycin (everolimus), 40-O-(3-hydroxyl)propyl-rapamycin, 40-O-[2-(2-hydroxyl)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these.

An implantable device including a coating described herein can be a stent that can be a metallic, biodegradable or nondegradable stent. The stent can be intended for neurovasculature, carotid, coronary, pulmonary, aorta, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION OF THE INVENTION

Provided herein is a coating on a medical device, such as a stent, that includes a construct having an elastic primer layer. The elastic primer layer will lower the stress generated in the coating, e.g., stress generated in the drug depot layer (which is also referred to as drug reservoir layer). An elastic primer layer can absorb more of elastic strain energy upon deployment of the medical device, e.g., stent expansion, and therefore shield the more brittle part of the coating from the stress. Generally, the elastic or elastomeric primer enables the biocompatible coating, which controls the release of drug, to be less robust that it has to be when no primer is present. This construct therefore will minimize or eliminate the cracking in the coating (e.g., the matrix layer or the drug depot layer). In addition, interfacial shear stress between the drug depot layer and the surface of the medical device, had the depot layer been directly deposited on the surface of the medical device, and thus, the use of an elastic layer will minimize or eliminate the occurrence of drug depot layer delamination.

In some embodiments, the elastic primer layer can allow the use of polymers with lower molecular weight to form the matrix layer or drug depot layer so as to form a coating having a faster degradation rate. Some examples of lower molecular weight polymers are PEA-40 polymers, which are poly(ester amide) polymers having a cyclic structure. As used herein, the term "low molecular weight" or "lower molecular weight" refers to that molecular weight at and below which the polymer is too brittle to survive stent crimping and stent expansion for deployment. This molecular weight will vary from polymer to polymer. Some polymers are always too brittle to be useful, while others are too brittle only if below their "entanglement" molecular weight. The term "entanglement" molecular weight can be explained as below:

If one plots log of the zero shear rate viscosity versus log of the molecular weight two distinct power-law regimes are observed:
1) $\eta_0 = K\,(MW)^P$
where at low molecular weights P=1 and $\eta_0 = K\,MW$, at high molecular weights P=3.4 and $\eta_0 = K\,(MW)^{3.4}$, and where $\eta_0$ is the zero shear viscosity and MW is the molecular weight.

As a person of ordinary skill in the art would appreciate it, this value is different for different polymers.

2) The transition between these two regimes is the entanglement molecular weight ($M_e$).

Below the $M_e$, polymers are typically brittle. As the molecular weight is increased, the physical properties of the polymer continuously increase and then level off as the $M_e$ is exceeded (see, e.g., J. R. Fried, "Polymer Science and Technology", particularly FIGS. 11.14 and 11.17 and the description thereof; Bird, Armstrong, Hassager, "Dynamics of Polymeric Liquids Vol. 1", FIGS. 3.6-4 and 3.6-5 and the description thereof). The $M_e$ therefore distinguishes a polymer from and oligomer. Below the $M_e$, oligomers are brittle solids, white powder; flow behavior is similar to low-molecular weight materials; no normal forces are observed; and a wide range of Newtonian viscosity is observed in shear rate etc. Above $M_e$, polymers are robust solids, i.e. plastics with good engineering properties; and flow behavior becomes non-Newtonian with large strain rate and temperature dependencies, elasticity and large normal forces.

The drug depot layer can include any bioactive agent. In some embodiments, the bioactive agents can be paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl(4-amino-TEMPO), tacrolimus, dexamethasone, rapamycin, rapamycin derivatives, 40-O-(2-hydroxyl)ethyl-rapamycin (everolimus), 40-O-(3-hydroxyl)propyl-rapamycin, 40-O-[2-(2-hydroxyl)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these.

An implantable device including a coating described herein can be a stent that can be a metallic, biodegradable or nondegradable stent. The stent can be intended for neurovasculature, carotid, coronary, pulmonary, aorta, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

As used herein, the term "implantable device" and the term "medical device" are sometimes used interchangeably.

As used herein, the term "elastic" refers to the attribute pertaining to a soft, compliant, rubber-like material or any of various polymers having the elastic properties of natural rubber.

In some embodiments, the depot system can be a pure active agent without a polymeric carrier. When this design is used, usually it is hard to coat the bioactive itself onto a metal surface of the depot system, e.g., the depot system can have cracking. Applying an elastic layer onto the metal surface, and then applying to the elastic layer the pure bioactive agent can form the depot system without causing further cracking of the coating.

Elastic Polymers

Any elastic polymers can be used for forming the primer layer as long as they adhere will to the surface of the stent. Generally, an elastic polymer has a relatively long aliphatic chains (does not have to be an aliphatic chain—in general, an elastic polymer is one of high mw, above the entanglement molecular weight, and of high elongation (above 10%, but 30 to 300% or higher preferred and will typically have a Tg below ambient) in the polymer chain that allows the polymer to be flexible and can have a relatively low glass transition temperature ($T_g$). For example, an elastic polymer useful for forming an elastic primer layer described herein can have a Tg at about 50° C. or lower and lower is preferred along with high elongation.

In some embodiments, the elastic polymer is a poly(ester amide) (PEA) polymer. For example, the PEA polymer can be PEA-TEMPO. In some embodiments, the elastic polymer can be a biodegradable elastic polymer, as a polyester of an aliphatic acid. For example, the elastic polymer can be poly(butylene succinate) or poly(glycero-sebacinate). Any other elastic, absorbable polyester or non-absorbable polymers. Other examples are poly(ε-caprolactone), poly(trimethylene carbonate), poly(p-dioxanone), polyhydroxyalkanoates, poly(amino acids), etc.

In some embodiments, the elastic polymer can be copolymers with monomers from the polymers mentioned above. Some examples of such copolymers are polyester copolymers comprising units derived from a monomer selected from ester amide, butylene succinate, glycero-sebacinate, ε-caprolacteone, trimethylene carbonate, p-dioxanone, hydroxyalkanoates, amino acids, or combinations thereof.

In some embodiments, the elastic polymer can be a polycaprolactone (PCL) polymer or copolymers containing PCL.

In some embodiments, the elastic polymer defined herein can specifically exclude any of the particular polymers or copolymers described above.

Polycaprolactone Polymers

A PCL polymer can be used to form the elastic primer layer if the PCL polymer is an elastic polymer or to form the matrix layer or the drug depot layer. A PCL polymer is a polymer or copolymer comprising units having the following general formula wherein $R_1$, $R_2$, $R_3$ and $R_4$ are independently hydrogen, methyl, ethyl, a straight or branched C3-C12 alkyl or cycloalkyl, phenyl or phenylalkyl. $R_1$, $R_2$, $R_3$ and $R_4$ can independently include one ore more substituents such as halo groups (F, Cl, Br or I), amino, hydroxyl, carboxyl, or aliphatic such as methyl and ethyl.

wherein x and y are independent integers from 0 to about 20, e.g., 1, 2, 3, 4, 5, 6, 7, 8, 9, 10, 11, 12, 13, 14, 15, 16, 17, 18 or 19; and wherein n is an integer. Exemplary values for n is 2 to about 100,000.

In some embodiments, the PCL polymer defined above can specifically exclude a PCL polymer defined by any of specific combinations of $R_1$, $R_2$, $R_3$ and $R_4$, x, y, and n. For example, the PCL can specifically exclude a polymer or copolymer formed of glycolide or lactide.

PEA Polymers

A PEA polymer can be used to form the elastic primer layer or to form the matrix layer or the drug depot layer, depending on the elasticity or non-elasticity of the PEA polymer. The PEA polymers are a class of polymers that include at least one amide grouping and one ester grouping in the backbone of the polymer. Two examples of PEA polymers are PEA-TEMPO and PEA-Benzyl (PEA-Bz). Other PEA polymers can be readily formed. A general strategy of forming PEA polymers having a structure similar to PEA-Bz and PEA-TEMPO are described below:

(a) varying the leucine:lysine monomer ratio using the synthesis shown in Scheme I, below (e.g., forming a polymer having units derived predominantly from lysine monomer);

(b) removing the leucine or the lysine monomers entirely;

(c) replacing the leucine monomer with one based on another amino acid such as glycine, valine, alanine, isoleucine, or phenyl alanine;

(d) replacing the lysine monomer with one based on another amino acid such as tysorine, glutamic acid, or cysteine;

(e) substituting another diol for the 1,6-hexanediol. The diol can be, e.g., a C2 to C12 diol and can include branching, cyclic structures and/or unsaturation; and (f) substituting another diacid for the sebacic acid. The diacid can be, e.g., a C2 to C12 acid, aliphatic, cyclic, or with unsaturation.

For example, PEA polymers can include at least three building blocks: at least one amino acid, at least one diol, and at least one diacid. The diacid can be, e.g., a C2-C12 diacid, aliphatic or with unsaturation. The amino acid can be, for example, glycine, valine, alanine, proline, glutamine, methionine, leucine, isoleucine, or phenylalanine. An optional second amino acid can be included. The second amino acid can be, for example, lysine, tyrosine, tryptophan, arginine, histidine, glutamic acid, aspartic acid, threonine, serine, or cysteine. The second amino acid can contain a side group to enable the attachment of pharmacologically active compounds or property modifiers. PEA polymers with various physical and mechanical properties can be readily prepared by varying these components during synthesis.

In some embodiments, it is desirable to decrease or increase the $T_g$ of the PEA polymers. For example, decreasing the polymethylene chain length of the diol or diacid building block will increase the $T_g$. PEA polymers based on amino acids with optical rotation (e.g., enantiomerically pure) will have higher $T_g$ than those based on the corresponding racemic amino acids (D,L-isomers). PEA polymers synthesized from amino acids with symmetrical side substituents (e.g., valine, leucine, phenylalanine) will have higher $T_g$s than those synthesized from amino acids with nonsymmetrical side substituents (e.g., isoleucine). Amino acids with aromatic substituents (e.g., phenylalanine) tend to have higher $T_g$s.

Some examples of PEA polymers other than PEA-Bz or PEA-TEMPO are shown in Formulae 1-6.

-[-sebacinate-L-Leu-hexanediol-L-Leu-]$_m$-[-sebacinate-Lys TEMPO-]$_n$-   Formula 1, -[-sebacinate-L-Leu-hexanediol-L-Leu-]$_n$-   Formula 2, -[-adipate-L-Leu-hexanediol-L-Leu-]$_n$-   Formula 3A -[-sebacinate-L-Leu-butanediol-L-Leu-]$_n$-   Formula 3B, -[-adipate-L-Leu-butanediol-L-Leu-]$_n$-   Formula 3C, -[-sebacinate-L-Val-hexanediol-L-Val-]$_n$-   Formula 4A -[-sebacinate-L-Phe-hexanediol-L-Phe-]$_n$-   Formula 4B, -[-adipate-L-Val-butanediol-L-Val-]$_n$-   Formula 4C -[-adipate-L-Phe-butanediol-L-Phe-]$_n$-   Formula 4D -[-adipate-L-Leu-hexanediol-L-Leu-]$_m$-[-adipate-Lys-R]$_n$- R=benzyl ester or TEMPO   Formula 5A -[-sebacinate-L-Leu-butanediol-L-Leu-]$_m$-[-sebacinate-Lys-R]$_n$- R=benzyl ester or TEMPO   Formula 5B -[-adipate-L-Leu-butanediol-L-Leu-]$_m$-[-adipate-Lys-R]$_n$- R=benzyl ester or TEMPO   Formula 5C -[-sebacinate-L-Val-hexanediol-L-Val-]$_m$-[-sebacinate-Lys-R]$_n$- R=benzyl ester or TEMPO   Formula 5D -[-sebacinate-L-Phe-hexanediol-L-Phe-]$_m$-[-sebacinate-Lys-R]$_n$- R=benzyl ester or TEMPO   Formula 5E -[-adipate-L-Val-butanediol-L-Val-]$_m$-[-adipate-Lys-R]$_n$- R=benzyl ester or TEMPO   Formula 5F

-[-adipate-L-Phe-butanediol-L-Phe-]$_m$-[-adipate-Lys-R]$_n$- R=benzyl ester or TEMPO   Formula 5G -[-sebacinate-L-Leu-hexanediol-L-Leu-]$_m$-[-sebacinate-Lys R]$_n$- R=methyl, ethyl, or propyl   Formula 6

The PEA polymers having a first amino acid and optionally a second amino acid can have different ratios of the two amino acids, ranging from, e.g., 1/99 or vice versa. For example, the ratio of the amino acids, lysine and leucine, in PEA polymers of Formulae 1 and 5A-5G can range from 1/99 to 99/1, e.g., 1/9, 1/4, 3/7, 2/3, 1/1, 3/2, 7/3, 4/1, or 9/1. The first and the second amino acids can be any of the natural amino acids or unnatural amino acids. Representative natural amino acids can be, for example, valine, leucine, phenylalanine, isoleucine, glycine, glutamic acid, alanine, lysine, tyrosine, methionine, aspartic acid, arginine, serine, threonine, cysteine, asparagine, proline, tryptophan, histidine, and combinations thereof. Representative unnatural amino acids include, but are not limited to, 2-cyclohexylglycine, 2-amino-3,3-dimethyl butyric acid, 2-phenyl glycine, 6-aminocaproic acid, 4-aminobutyric acid, 2-aminoadipic acid, 3-aminobutyric acid, 3-amino-3-phenyl propionic acid, and 1-azetidine-3-carboxylic acid. A compendium of unnatural amino acids may be found in ChemFiles, Unnatural Amino Acids Vol. 2, No. 4 and ChemFiles Unnatural Amino Acids, Vol. 1, No. 5 published by Sigma Aldrich Corporation of St. Louis, Mo.

The PEA polymers described herein can be made by condensation polymerization using, among others, diamino subunits and dicarboxylic acids. The preparation of one example of these PEAs is shown in Scheme I, where the dicarboxylic acid is converted to an active di-p-nitrophenyl derivative.

Scheme 1

Coating Construct

An elastic primer layer can be included in any coating. In some embodiments, the coating can include a matrix layer on top of the elastic primer layer without a bioactive agent (e.g., drug). In some embodiments, coating can include a drug depot layer, which is also referred to as a reservoir layer, that includes at least one bioactive agent (e.g., drug). The coating can also include a topcoat and/or a barrier layer on top of the matrix layer or drug depot layer.

The elastic primer layer can have be thin or thick (thin is usually preferred), depending on the design and/or the need of the coating. For example, the elastic primer layer can absorb less or more elastic strain energy, depending upon the thickness of the elastic primer layer or thickness of the elastic primer layer in relation to the total thickness of the coating. In some embodiments, the thickness of the elastic primer layer in relation to the total thickness of the coating can be expressed by the weight ratio of the elastic polymer forming the elastic primer layer to the total weight of polymer(s) forming the coating. In some embodiments, such weight ratio can be from about 1:19, about 2:18, about 3:17, about 4:16, about 5:15, about 6:14, about 7:13, about 8:12, about 9:11, about 10:10, about 11:9, about 12:8, about 13:7, about 14:6, about 15:5, about 16:4, about 17:3, about 18:2, or about 19:1 to about 10:1. In some embodiments, the weight ratio of the elastic polymer forming the elastic primer layer to the total weight of polymer(s) forming the coating can be about 5:1 to about 1:5.

Biocompatible Polymer

In some embodiments, the coating described herein can include a polymer that is different from the elastic polymers described above. Some representative examples of such polymers include, but are not limited to, non-elastic PEA polymers, ethylene vinyl alcohol copolymer (commonly known by the generic name EVOH or by the trade name EVAL), poly(hydroxyvalerate), non-elastic polycaprolactone polymers, poly(lactide-co-glycolide), poly(hydroxybutyrate), poly(hydroxybutyrate-co-valerate), polydioxanone, poly(glycolic acid-co-trimethylene carbonate), polyphosphoester urethane, poly(amino acids), polycyanoacrylates, poly(trimethylene carbonate), poly(iminocarbonate), polyurethanes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as vinylidene fluoride based home or copolymer under the trade name Solef™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacinate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose, copolymers of these polymers with poly(ethylene glycol) (PEG), or combinations thereof.

In some embodiments, the biocompatible polymer can be poly(ortho esters), poly(anhydrides), poly(glycolic acid), copolymers of poly(lactic) and glycolic acid, poly(L-lactide), poly(D,L-lactide), poly(glycolide), poly(D,L-lactide-co-glycolide), poly(L-lactide-co-glycolide), poly(phospho esters), poly(trimethylene carbonate), poly(oxaesters), poly(oxaamides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly(ethylene glycol) (PEG), or combinations thereof.

In some other embodiments, the biocompatible polymer can exclude any one or more of the polymers provided above.

Bioactive Agents

The coating described herein can include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxyl) ethyl-rapamycin (everolimus), and its functional or structural derivatives, paclitaxel and its functional and structural derivatives. Examples of rapamycin derivatives include methyl rapamycin (ABT-578), 40-O-(3-hydroxyl)propyl-rapamycin, 40-O-[2-(2-hydroxyl)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anti-coagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl(4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Devices

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE® and ENDOTAK®, available from Abbott Vascular, Santa Clara, Calif.). The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth example. All parameters and data are not to be construed to unduly limit the scope of the embodiments of the invention.

Example 1

Figure 1:
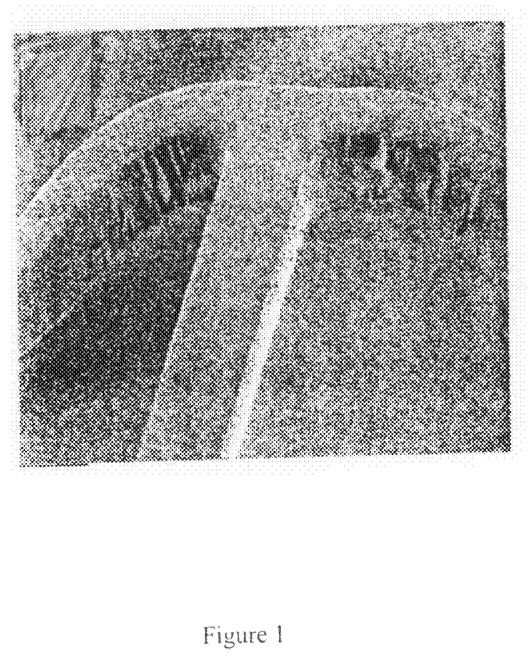
FIG. 1 shows the scanning electron microscope (SEM) image of a coating formed of PEA-40 polymer and everolimus (drug:polymer=1:3).

As control, a coating including PEA-40 and everolimus (drug:polymer=1:3) was formed on a stent and then subjected to simulated use test. The scanning electron microscope (SEM) image of the coating is shown in FIG. 1, which shows a poor coating integrity with cracks.

Figure 2:
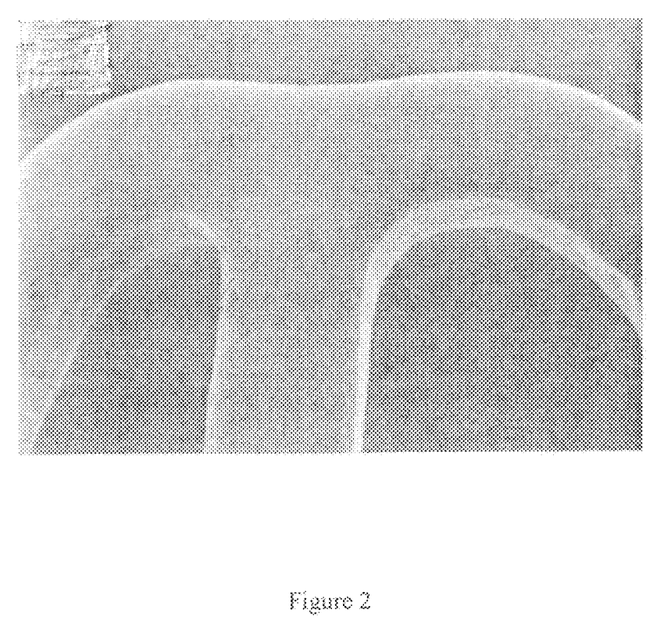
FIG. 2 shows the SEM image of a coating having an elastic PEA-TEMPO primer layer (1 µm) and a matrix layer (2 µm) formed of PEA-40.

A coating including an elastic PEA-TEMPO primer layer (1 μm) and a matrix layer (2 μm) formed of PEA-40 was formed on a stent and subjected to simulated use test. The SEM image of the coating is shown in FIG. 2, which shows a coating of good integrity with no crack.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. An implantable medical device comprising a coating, the coating comprising:
   an elastic primer layer comprising a polymer formed on a surface of an implantable medical device, and the polymer being poly(butylene succinate); and
   a matrix layer or a drug depot layer on top of the primer layer;
   wherein the matrix layer or the drug depot layer comprises at least one bioactive agent.

2. The implantable medical device of claim 1, wherein the primer layer further comprises an elastic polycaprolactone (PCL) polymer.

3. The implantable medical device of claim 1, wherein the primer layer further comprises an elastic polyester polymer.

4. The implantable medical device of claim 1, wherein the drug depot layer is free of polymers.

5. The implantable medical device of claim 1, which is a stent.

6. The implantable medical device of claim 2, which is a stent.

7. The implantable medical device of claim 3, which is a stent.

8. The implantable medical device of claim 1, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl(4-amino-TEMPO), tacrolimus, dexamethasone, rapamycin, 40-O-(2-hydroxyl)ethyl-rapamycin (everolimus), 40-O-(3-hydroxyl)propyl-rapamycin, 40-O-[2-(2-hydroxyl)ethoxy]ethyl-rapamycin, 40-O-tetrazole-rapamycin, 40-epi-(N1-tetrazolyl)-rapamycin (ABT-578), zotarolimus, γ-hiridun, clobetasol, mometasone, dexamethasone, dexamethasone acetate, pimecrolimus, imatinib mesylate, midostaurin, and combinations of these.

9. The stent of claim 5, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), tacrolimus, dexamethasone, rapamycin, 40-O-(2-hydroxyl)ethyl-rapamycin (everolimus), 40-O-(3-hydroxyl)propyl-rapamycin, 40-O-[2-(2-hydroxyl)ethoxy]ethyl-rapamycin, 40-O-tetrazole-rapamycin, 40-epi-(N1-tetrazolyl)-rapamycin (ABT-578), zotarolimus, γ-hiridun, clobetasol, mometasone, dexamethasone, dexamethasone acetate, pimecrolimus, imatinib mesylate, midostaurin, and combinations of these.

10. The implantable medical device of claim 1, wherein the polymer of the primer layer has a molecular weight above the entanglement molecular weight.

* * * * *